United States Patent [19]

Bakshi et al.

[11] Patent Number: 5,578,726
[45] Date of Patent: *Nov. 26, 1996

[54] PROCESS FOR PRODUCING 7 β-SUBSTITUTED-4-AZA-5 α-ANDROSTAN-3-ONES

[75] Inventors: Raman K. Bakshi, Edison; Gary H. Rasmusson, Watchung, both of N.J.

[73] Assignee: Merck & Co., Inc., Rahway, N.J.

[ * ] Notice: The term of this patent shall not extend beyond the expiration date of Pat. No. 5,237,064.

[21] Appl. No.: 335,791

[22] PCT Filed: May 11, 1993

[86] PCT No.: PCT/US93/04443

§ 371 Date: Nov. 10, 1994

§ 102(e) Date: Nov. 10, 1994

[87] PCT Pub. No.: WO93/23376

PCT Pub. Date: Nov. 25, 1993

Related U.S. Application Data

[63] Continuation of Ser. No. 886,049, May 20, 1992, Pat. No. 5,237,064.

[51] Int. Cl.$^6$ .................................... C07J 73/00
[52] U.S. Cl. ................ 546/77; 540/2; 540/15; 540/107; 546/78; 546/14; 562/499
[58] Field of Search .................... 540/2, 15, 109; 546/77, 14, 78; 562/499

[56] References Cited

U.S. PATENT DOCUMENTS

| | | | |
|---|---|---|---|
| 4,139,619 | 2/1979 | Chidsey, III . | |
| 4,220,775 | 9/1980 | Rasmusson et al. | 546/77 |
| 4,377,584 | 3/1983 | Rasmusson et al. | 546/77 |
| 4,760,071 | 7/1988 | Rasmusson et al. | 546/77 |
| 4,859,681 | 8/1989 | Rasmusson et al. | 546/77 |
| 4,888,336 | 12/1989 | Holt et al. | 514/278 |
| 5,049,562 | 9/1991 | Rasmusson et al. | 514/284 |
| 5,237,064 | 8/1993 | Bakshi et al. | 546/77 |
| 5,237,065 | 8/1993 | Holt | 546/77 |
| 5,278,159 | 1/1994 | Bakshi et al. | 546/77 |

FOREIGN PATENT DOCUMENTS

| | | |
|---|---|---|
| 0004949 | 10/1979 | European Pat. Off. . |
| 0155096 | 9/1985 | European Pat. Off. . |
| 0289327 | 11/1988 | European Pat. Off. . |
| 0314199 | 5/1989 | European Pat. Off. . |
| 93/23420 | 11/1993 | WIPO . |
| 93-23376 | 11/1993 | WIPO . |

OTHER PUBLICATIONS

Rasmusson et al. "Azasteroids: Structure–Activity Relationships for Inhibition of 5 α–Reductase and of Androgen–Receptor Binding", J. Med. Chem. 29 (11): 2298–2315 (1986).
Rasmusson et al. "Azasteroids as Inhibitors of Rat Prostatic 5 α–Reductase", J. Med. Chem. 27 (12): 1690–1701 (1984).
Stinson, "Prostate Drug Proscar Cleared for Marketing" Chem. Eng. News, Jun. 29, 1992, pp. 7–8.
Helliker, "Alopecia Sufferers Seek to Suffer Less, and Not in Silence,", Wall Street Journal, 7 Jun. 1991, pp. A1 and A7.
Diani et al., "Hair Growth Effects of Oral Administration of Finasteride, a Steroind 5 α–Reductase Inhibitor Alone and in Combination with Topical Minoxidil in the Balding Stumptail Macaque", J. Clin. Endocrin. and Metabl., 74(2):345–350 (1990).
Back et al., "N–Chloroazasteroids: A Novel Class of Reactive Steroid Analogues Preparation, Research with Thiols, and Photochemical Conversion to Electrophilic N–Acyl Imines", J. Org. Chem. 54: 1904–1910 (1989).
Back "Oxidation of Lactams and Alcohols with Benezene Selenic Anhydride", J. Org. Chem. 46: 1442–1446 (1981).

*Primary Examiner*—Donald G. Daus
*Attorney, Agent, or Firm*—Joanne M. Giesser; Melvin Winokur; Catherine D. Fitch

[57] ABSTRACT

Described is a new process for producing 7β-substituted-4-aza-5α-androstan-3-ones and related compounds which are 5α-reductase inhibitors, consisting of reducing the corresponding androsteneone with lithium and liquid ammonia, contacting the product with an isomerizing agent, oxidizing the product to a seco acid and reacting that seco acid with an amine to cyclize to form 4-aza-5α-androstan-3-ones.

9 Claims, No Drawings

PROCESS FOR PRODUCING 7 β-SUBSTITUTED-4-AZA-5 α-ANDROSTAN-3-ONES

This is a Section 371 of PCT/US93/04443 filed May 11, 1993 which is a continuation-in-part of Ser. No. 07/886,049, filed May 20, 1992, now U.S. Pat. No. 5,237,064.

BACKGROUND OF THE INVENTION

The present invention is directed to a new process for preparing 7β-substituted-4-aza-5α-androstan-3-ones and related compounds and the use of such compounds as 5α-reductase inhibitors.

DESCRIPTION OF THE PRIOR ART

The art reveals that certain undesirable physiological manifestations, such as acne vulgaris, seborrhea, female hirsutism, male pattern baldness and benign prostatic hypertrophy, are the result of hyperandrogenetic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethylisobutyranilide. See Neri, et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It is now known in the art that the principal mediator of androgenic activity in some target organs is 5α-dihydrotestosterone, and that it is formed locally in the target organ by the action of testosterone-5α-reductase. It is also known that inhibitors of testosterone-5α-reductase will serve to prevent or lessen symptoms of hyperandrogenic stimulation.

A number of 4-aza steroid compounds are known in the art as 5α-reductase inhibitors. For example, see U.S. Pat. Nos. 4,377,584, 4,220,775, 4,859,681, 4,760,071 and the articles J. Med. Chem. 27, p. 1690–1701 (1984) and J. Med. Chem. 29, 2998–2315 (1986) of Rasmusson, et al., U.S. Pat. No. 4,845,104 to Carlin, et al., and U.S. Pat. No. 4,732,897 to Cainelli, et al. which describe 4-aza-17β-substituted-5α-androstan-3-ones said to be useful in the treatment of DHT-related hyperandrogenetic conditions.

However, despite the suggestion in the prior art that hyperandrogenetic diseases are the result of a single 5α-reductase, there are reports regarding the presence of other 5α-reductase isozymes in both rats and humans. For example, in human prostate, Bruchovsky, et al. (See J. Clin. Endocrinol. Metab. 67,806–816, 1988) and Hudson (see J. Steroid Biochem. 26, p 349–353, 1987) found different 5α-reductase activities in the stromal and epithelial fractions. Additionally, Moore and Wilson described two distinct human reductases with peaks of activities at either pH 5.5 or pH 7–9. (See J. Biol. Chem. 251, 19, p. 5895–5900, 1976.)

Recently, Andersson and Russell isolated a cDNA which encodes a rat liver 5α-reductase (see J. Biol. Chem. 264 pp. 16249–55 (1989). They found a single mRNA which encodes both the liver and prostatic reductases of rats. The sequence of this rat gene was later used to select a human prostatic cDNA encoding a 5α-reductase termed "5α-reductase 1" (See Proc. Nat'l. Acad. Sci. 87, p. 3640–3644, 1990.)

More recently, a second, more adundant reductase (5α-reductase 2) has been cloned from human prostate with properties identified with the form found in crude human prostatic extracts. (See Nature, 354, p. 159–161, 1991.)

Further, "Syndromes of Androgen Resistance"—The Biology of Reproduction, Vol. 46, p. 168–173 (1992) by Jean O. Wilson indicates that the 5α-reductase 1 enzyme may be associated with hair follicles.

Thus, the art supports the existence of at least two genes for 5α-reductase and two distinct isozymes of 5α-reductase in humans. Both forms are present in prostatic tissue in which, 5α-reductase 2, is the more abundant, and the other isozyme, 5α-reductase 1, is believed to be more abundant in scalp tissue.

In the treatment of hyperandrogenetic disease conditions, e.g. benign prostatic hyperplasia (BPH) it would be desirable to have one drug entity which is active against both enzymes 1 and 2 in the prostate to substantially inhibit dihydrotesterone (DHT) production. Alternatively, it would be desirable to have a drug entity which is highly selective for inhibiting the scalp associated enzyme 5α-reductase 1, for use in treating diseases of the skin and scalp, e.g. ache and alopecia. This latter drug could also be used in combination with PROSCAR® (finasteride) which is highly selective for the prostatic enzyme 5α-reductase 2 for combination therapy in the treatment of BPH.

New processes are continuously being searched for which are more efficient and environmentally acceptable for producing 7-beta substituted androstane-3-ones, which are active against both alpha reductase enzymes 1 and 2.

SUMMARY OF THE INVENTION

The present invention discloses a novel process for preparing 7β-substituted-4-aza-5α-androstan-3-one compounds which are useful for inhibiting the 5α-reductase isozymes 1 and 2 and are particularly effective in selectively inhibiting the 5α-reductase-1 associated with the scalp and dually inhibiting both isozymes 1 and 2 in the oral, parenteral or topical treatment of benign prostatic hyperplasia, acne, female hirsutism, male pattern baldness, androgenic alopecia, prostatitis, and the prevention and treatment of prostatic carcinoma.

In accordance with the present invention there is provided a process comprising the step of:

a) contacting the compound IV, where Alk is

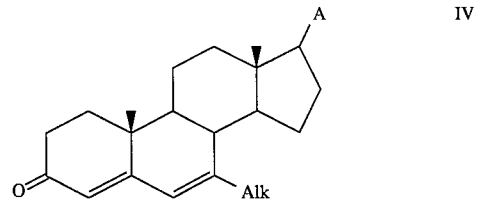

IV $C_1$–$C_4$ alkyl, allyl, and $C_3$–$C_6$ cycloalkyl, and A is a substituent inert under the reaction conditions, with a reducing system comprised of: metallic lithium and liquid ammonia in an inert organic solvent therefor at a temperature in the range of about −45° to −78° C. for a sufficient time to stereoselectively produce the 7-beta compound V:

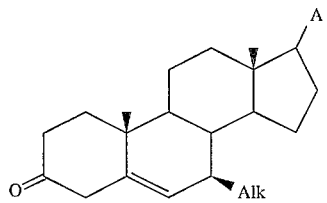
V

Further provided in the process is the step of:

b) contacting compound V with a double bond isomerization agent in an inert organic solvent therefor, at a temperature of 40° to 65° C., under conditions in which the radical A is inert, for a sufficient time to form the isomerized compound VI.

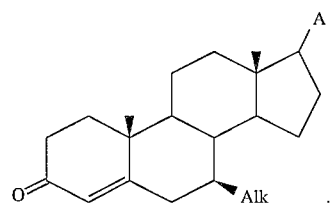
VI

Also provided in the process is the step of:

(c) contacting compound VI with an oxidizing agent in an inert solvent therefor, at a temperature in the range of 23° to 80° C., under conditions in which radical A is inert, for a sufficient time to form the seco acid VII:

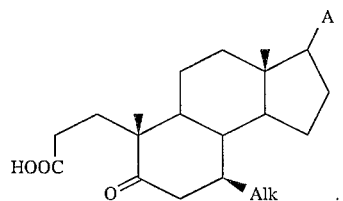
VII

In addition, there is provided the step of:

(d) contacting the seco acid compound VII with an amine of the formula: R—NH$_2$, wherein R is H, C$_1$–C$_4$ alkyl, benzyl or allyl, at a temperature of from 100° to 200° C. in an inert solvent therefor, under conditions in which A is inert, to form the 4-aza-steroid VIII:

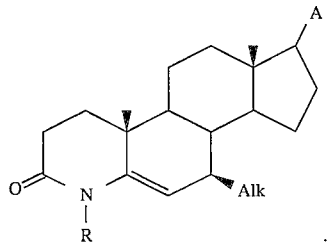
VIII

Provided also in the process is the step of:

(e) contacting VIII with a platinum catalyst in an inert organic solvent, at room temperature, under conditions where A is inert, for a sufficient time to form the 7-Alk 4-aza steroid IX:

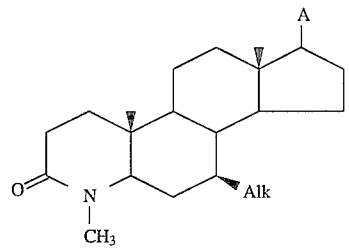
IX

Specific embodiments of the process is where Alk is methyl; the reducing system is comprised of metallic lithium and liquid ammonia; the process is carried out in the temperature range which is −78° to −45° C.

Also provided is the overall process comprising the steps of:

a) contacting the compound IV, where Alk is

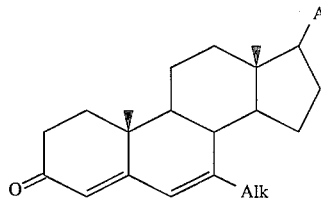
IV

C$_1$–C$_4$ alkyl, allyl and C$_3$–C$_6$ cycloalkyl, and A is a substituent inert under the reaction conditions, with a reducing system comprised of: metallic lithium and liquid ammonia in an inert organic solvent therefor at a temperature in the range of about −45° to −78° C. for a sufficient time to stereoselectively produce the 7-beta compound V:

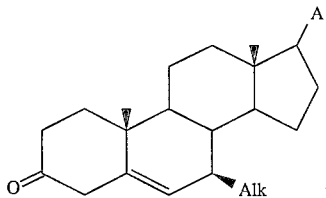
V ;

b) contacting compound V with a double bond isomerization agent in an inert organic solvent therefor, at a temperature of 40° to 65° C., under conditions in which the radical A is inert, for a sufficient time to form the isomerized compound VI.

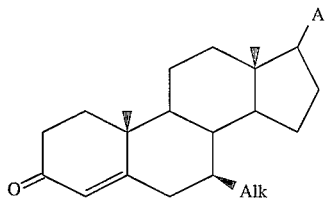
VI ;

(c) contacting compound VI with an oxidizing agent in an inert solvent therefor, at a temperature in the range of 23° to 80° C., under conditions in which radical A is inert, for a sufficient time to form the seco acid VII:

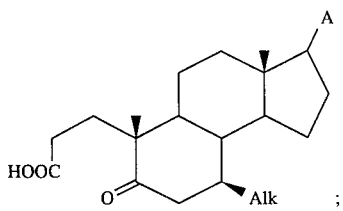

VII (d) contacting the seco acid compound VII with an amine of the formula: R—NH$_2$, wherein R is H, C$_1$–C$_4$ alkyl, benzyl or allyl, at a temperature of from 100° to 200° C. in an inert solvent therefor, under conditions in which A is inert, to form the 4-aza-steroid VIII:

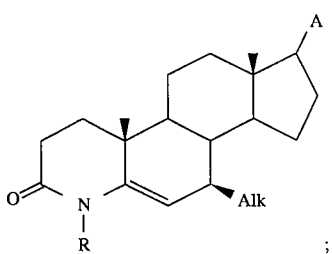

VIII (e) contacting VIII with a platinum catalyst in an inert organic solvent, at room temperature, under conditions where A is inert, for a sufficient time to form the 7-Alk 4-aza steroid IX:

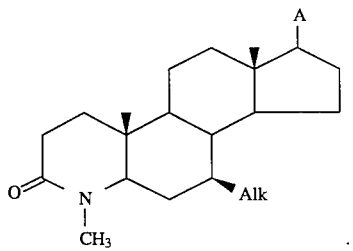

IX

DETAILED DESCRIPTION OF THE INVENTION AND PREFERRED EMBODIMENTS

By the term "C$_1$–C$_4$ alkyl" as used herein, is meant to include: e.g. methyl, ethyl, propyl, isopropyl, n-butyl, sec-butyl, isobutyl and t-butyl.

By the term "C$_3$–C$_6$ cycloalkyl" as used herein is meant to include cyclopropyl, cyclobutyl, cyclopentyl, cyclohexyl.

The process of this invention is illustrated in the following Flowsheets:

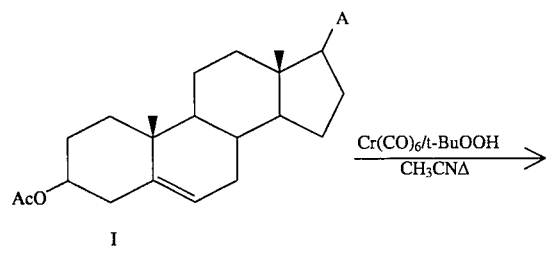

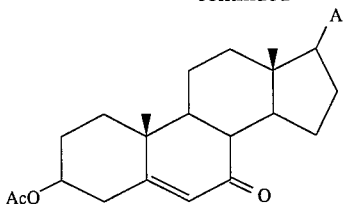

II

Alk Mg Cl / THF/24 h →

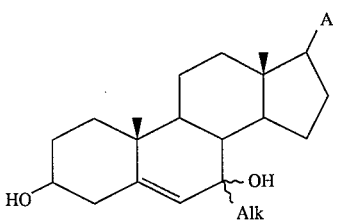

III

Al(OiPr)$_3$/C$_6$H$_{10}$O/ Toluene/Δreflux →

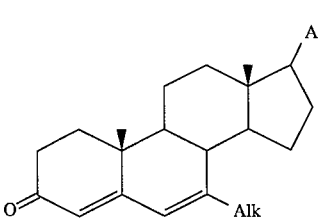

IV

Li/THF/ NH$_3$/Toluene/–78° →

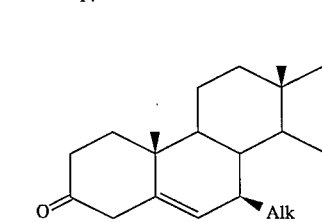

V

THF/DBU/Δ reflux →

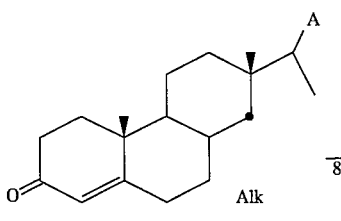

VI

KMnO$_4$/ NaIO$_4$/t-Bu—OH/ 80° C./H$_2$O/Δ/Na$_2$CO$_3$ →

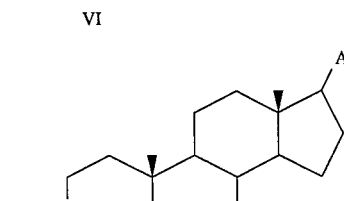

VII

NaOAc CH$_3$NH$_3$Cl/ CH$_2$OHCH$_2$OH/Δ →

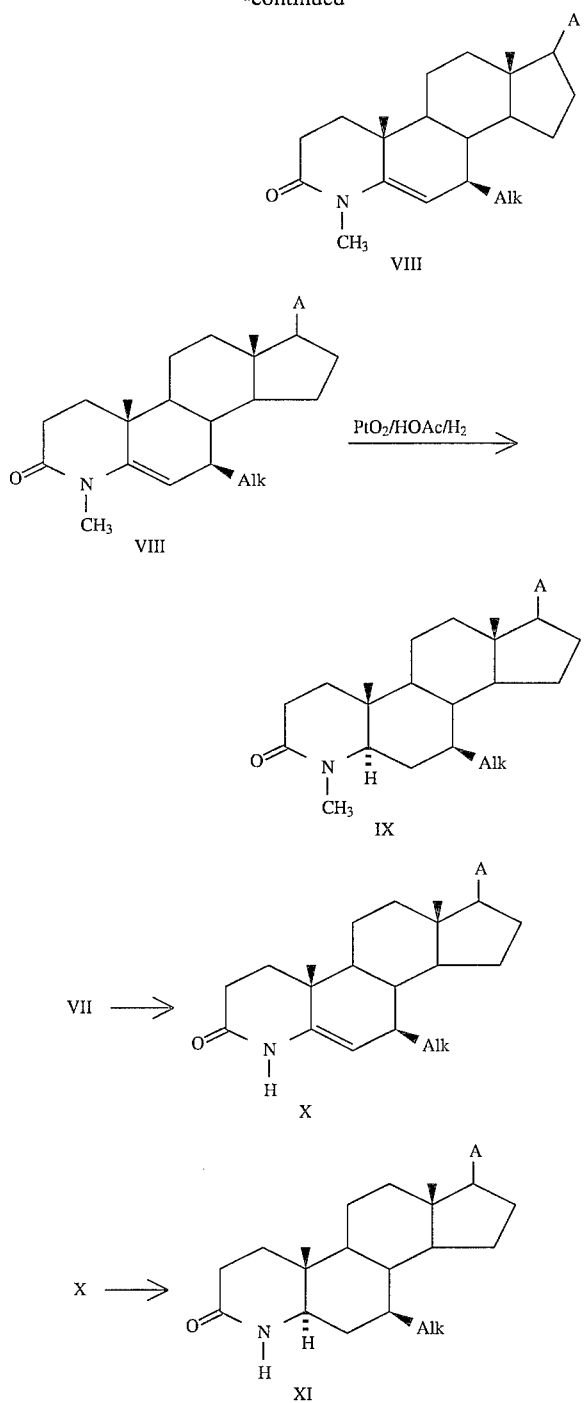

7-Beta Alkyl-17-A Series

The compounds produced by the instant invention also include a 7β alkyl group, e.g. methyl, ethyl, isopropyl, t-butyl, allyl, where A is defined below, can be prepared by the procedure outlined in The General Flowsheet.

The term "Alk" as used herein being the 7-beta substituent in the formula signifies $C_1$–$C_4$ linear or branched alkyl, e.g. methyl, ethyl, propyl, isopropyl, n-butyl, sec-butyl, isobutyl, t-butyl, and cycloalkyl.

The "Alk" substituent can be introduced onto the B ring of the 4-aza steroid generally by the application of an organometallic carbonyl addition reaction, e.g. the Grignard reaction in which the 7-carbonyl group can be reacted with the Grignard reagent containing "Alk" as the R radical in RMgX. Also applicable in the process are carbonyl addition reactions utilizing lithium and zinc organometallic reagents which are known in the art.

The term "A" is the 17-substituent which can be any substituent preferably inert and non-interfering under the particular reaction conditions of each step outlined in the following General Flowsheet.

The A group can also be a protected hydroxy or protected amino group which undergoes the indicated reaction sequence and then is subsequently removed, or it can also be removed during a particular step providing it does not interfere with the indicated reaction. For example, where A is 17-0-TBDMS, i.e., t-butyldimethylsilyloxy, the silyl protecting group can be removed during e.g., the ring closure step of the seco acid VII to the 4-aza steroid VIII, such that the subsequent steps are performed on the 17-OH compound. Also, the starting A group can be a precursor to the finally desired A group and be converting thereto concurrently in one of the steps. For example, where A contains a double bond, e.g., a stigmasterol analog, the double bond in the 17-side chain may also be oxidized during the seco acid formation in going form VI to VII.

Representative examples of the 17-A group include H, protected hydroxy, e.g. dimethyl-t-butyl silyloxy, hydroxy, protected amino, e.g. acetylamino, amino, $C_1$–$C_{10}$ alkyl, e.g. methyl, ethyl, 6-methyl-hept-2-yl (cholestanyl 17-side chain), stigmasterol side chain, aryl substituted $C_1$–$C_{10}$ alkyl, e.g. omega-phenylpropyl, heteroaryl substituted $C_1$–$C_{10}$ alkyl, e.g. omega-(a-pyridyl)-butyl, carboxylic ester, e.g. carbomethoxy, carboxamide, e.g. N,N-diisopropyl carboxamide, carboxylic acid, carbamates, e.g. t-butylcarbonylamino ureas, e.g. n-t-butylcarbonylamino, ethers, e.g. n-butyloxy- and the like.

The starting materials for the process generally are the 3-acetoxy-androst-5-enes which are known and available in the art.

As seen in the Flowsheet, using general formulas, where A is described above, the starting 3-acetoxy-androst-5-en-17-A I is oxidized to the corresponding 5-en-7-one II by treatment with e.g. hydrogen t-butyl peroxide and chromium hexacarbonyl in e.g. acetonitrile, at reflux. Other solvents which can be used include propionitrile, butyronitrile. The temperature for the reaction is generally carried out with range of 40° to 85° C. and the reaction is carried out under dry conditions and generally requires about 24 hours for completion.

The Alk group, e.g. methyl, ethyl, allyl, phenyl, can be introduced at this point by an organometallic carbonyl addition reaction, e.g. Grignard reaction using e.g., methyl, allyl or cycloalkyl magnesium chloride in e.g., anhydrous THF at 0°–23° C. to produce the 7-Alk-7-hydroxy adduct III. The Grignard reaction conditions are conventional and include the use of methyl magnesium chloride, ethyl magnesium bromide, allyl magnesium chloride, cyclopropyl magnesium bromide, and the like. Other usable dry solvents include diethyl ether, dimethoxyethane, di-n-butyl ether. The reaction is conducted under dry conditions generally in the temperature range of 0° to 40° C. Generally, the reaction requires about 6 to 24 hours for completion. Other organometallic carbonyl addition reactions can be used.

The adduct III is then oxidized with e.g. aluminum isopropoxide and cyclohexanone (Oppenauer oxidation conditions) in e.g. refluxing toluene solvent to produce the 7-alkyl-4,6-dien-3-one IV. Other reagents which can be used are aluminum ethoxide or aluminum t-butoxide. Other solvents which can be used are methylethylketone and xylene. The temperature range is generally in the range of 60° to 120° C., the reaction carried out under anhydrous conditions and generally requires about 2 to 24 hours for completion.

The next step is a key step in which the Grignard adduct IV is reduced with metallic lithium, liquid ammonia, THF and toluene at −78° C. to stereoselectively yield the 7-beta-alkyl-5-en-3-one V. Other metals which can be used in this reduction are: sodium, potassium, and calcium. Other amines which can be used are methylamine and ethylamine. Other solvents which can be used are: n-butylether, and dimethoxyethane. The reaction is generally carried out under anhydrous conditions in the temperature range of 23° C. to −78° C. and requires about 2–10 hours to go to completion.

In the next step the delta-5 double bond is isomerized to the 4-ene VI by the use of DBU (1,8-diazabicyclo[5.4.0]undec-7-ene) in, e.g. refluxing tetrahydrofuran (THF) to produce 7-alkyl 4-en-3-one. Other isomerization reagents which can be used include: diisopropylethylamine and DBN (Aldrich), being 1,5-diazabicyclo[4.3.0]non-5-ene. Other solvents which can be used include: toluene, dimethylether. The reaction is generally carried out under dry conditions at a temperature range of 40° to 65° C. and generally requires 1–2 hours for completion.

The A Ring is next cleaved by treatment with e.g. potassium permanganate, sodium periodate in e.g., t-butylalcohol at 80° C. to produce the corresponding seco-acid VII. Other oxidation reagents which can be used include ruthenium tetraoxide and ozone. Other solvents which can be used are: $CH_3CN$, $CCl_4$, MeOH and $CH_2Cl_2$. The reaction generally requires about 2 to 4 hours to proceed to completion.

Treatment of the seco-acid with an appropriate amine e.g., methylamine hydrochloride and sodium acetate in ethylene glycol at 180° C., yields e.g., the 4-methyl-4-aza-androst-5-en-3-one VIII. Other amines which can be used are ethylamine, ammonium acetate, substituted benzylamines, e.g. 4-methoxybenzylamine, and the like. Other solvents applicable in the reaction include: acetic acid, xylene. The reaction is generally carried out at a temperature in the range of 100° to 200° C. and generally requires about 2–8 hours to proceed to completion.

Structure VIII in turn is catalytically hydrogenated with e.g., Pt, to reduce the 5-delta double bond to produce the 5α-hydrogen compound IX. The solvent for the reduction is usually acetic acid but also useful is EtOH. The catalysts for this hydrogenation also include Pd/C and noble metals e.g. nickel. The hydrogenation is usually carried out in a shaker hydrogenation apparatus at room temperature under a $H_2$ pressure of 40 to 2000 psig. and generally requires about 1–24 hours to proceed to completion.

The seco-acid VII can be similarly treated with ammonia generated from ammonium acetate to produce the corresponding N-H compound, X, which can then be analogously treated as above with catalytic Pt in a hydrogen atmosphere to produce the corresponding 5α-4N-H compound XI.

Throughout this series of reactions, the 17-A group should be inert or non-interfering to the individual reaction conditions for placing the 7-substituent onto the steroid B ring.

FLOWSHEET A

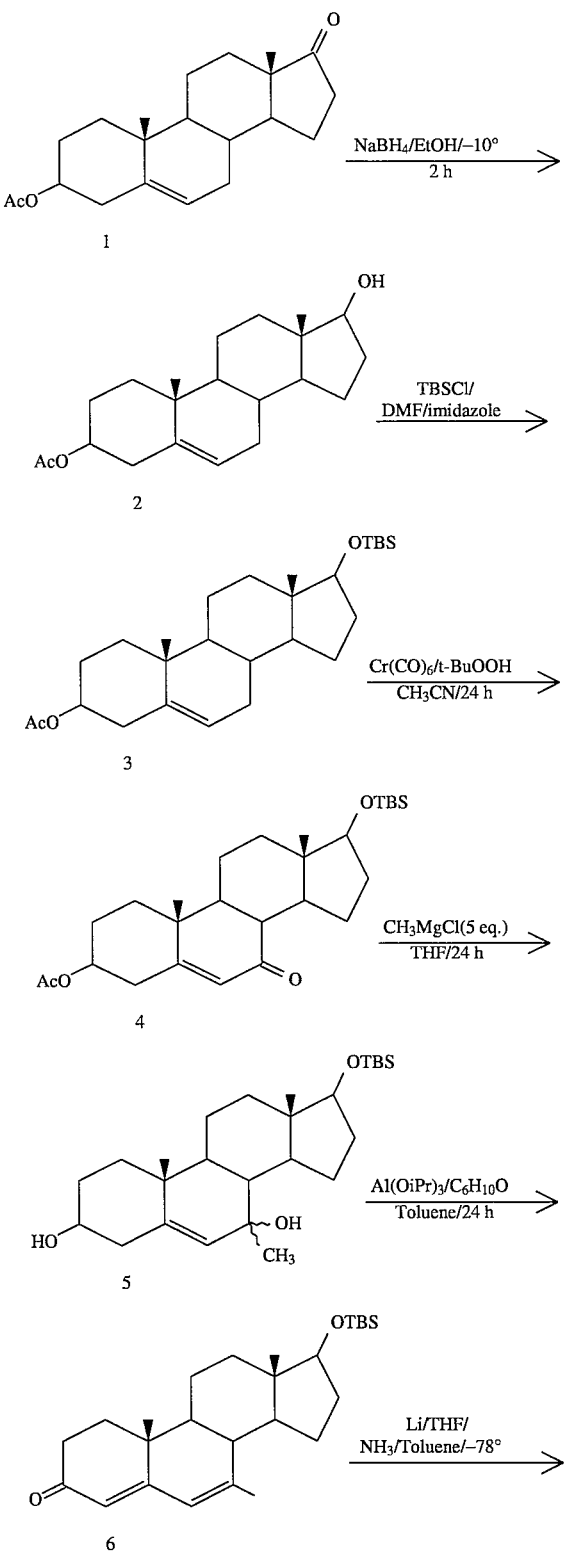

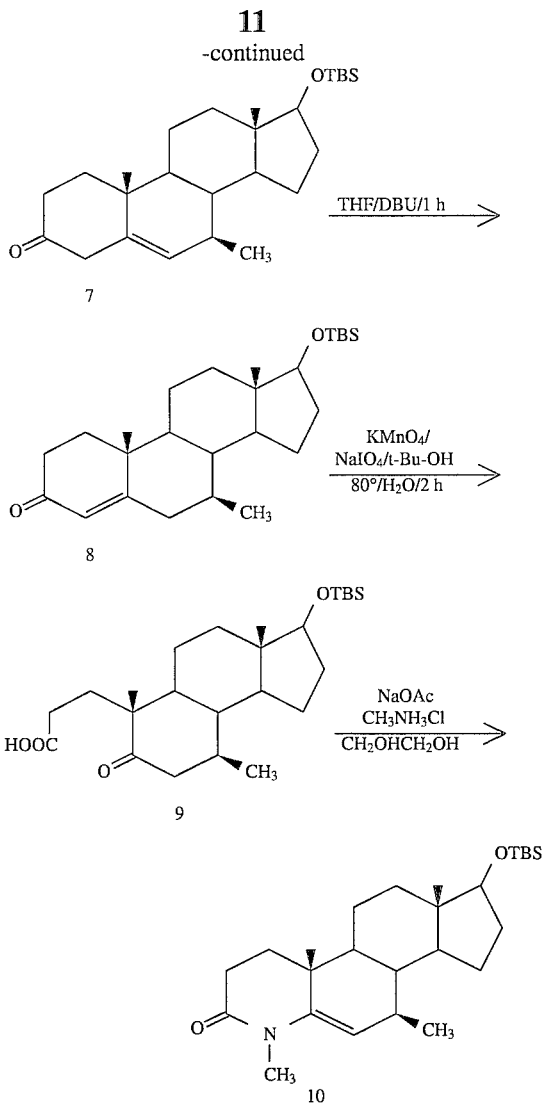

FLOWSHEET B

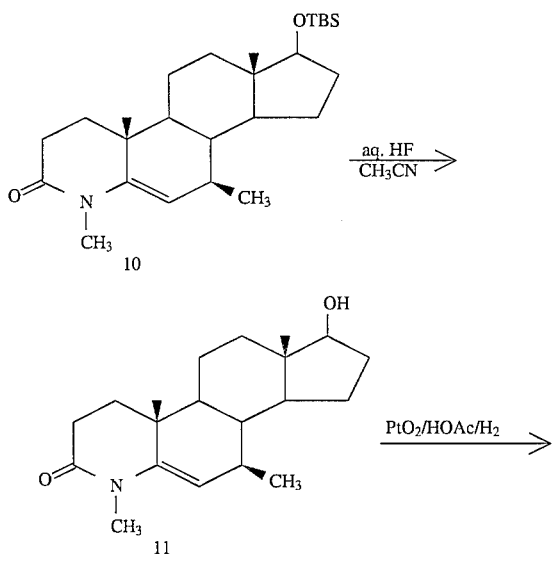

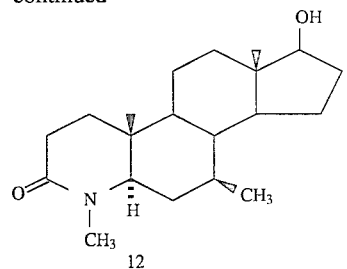

7-Beta Alkyl-17-Oxy-Androstanes

The process of the instant invention is also applicable, e.g. where 17-A is hydroxy or protected hydroxy. The appropriate 7β alkyl group, e.g. methyl, ethyl, isopropyl, can be introduced by the procedure outlined in Flowsheets A and B.

As seen in Flowsheet A, the 3-acetoxy-androst-5-en-17-one 1 is reacted with sodium borohydride in a suitable solvent, e.g. ethanol, at −10° C. to stereo-specifically reduce the 17-ketone to the 17β-ol 2. The 17-hydroxy group is protected with the TBS group (t-butyldimethylsilyl) by reacting TBS chloride with 2 in a suitable solvent, e.g. DMF in the presence of the proton acceptor, e.g. imidazole, at room temperature, to form 3.

Following the hydroxy protection, this compound is oxidized in the seven position to the corresponding 5-en-7-one 4 by treatment of 3 with hydrogen t-butyl peroxide and chromium hexacarbonyl in e.g. acetonitrile, at reflux. The alkyl group, e.g. methyl, can be introduced at this point by a Grignard reaction using e.g., methyl magnesium chloride in anhydrous THF at 0°–10° C. to produce the 7-methyl-7-hydroxy adduct 5. This Grignard product is then oxidized with aluminum isopropoxide and cyclohexanone (Oppenauer oxidation conditions) in refluxing toluene solvent to produce the 7-methyl-4,6-dien-3-one 6. This in turn is reduced using metallic lithium, in liquid ammonia, THF and toluene at −78° C. to selectively yield the 7-beta-methyl-5-en-3-one 7. In the next step the delta-5 double bond is isomerized to the 4-ene by use of DBU (1,8-diazabicyclo[5.4.0]undec-7-ene) in refluxing tetrahydrofuran (THF) to produce the 4-en-3-one, 8. The A Ring is next cleaved by treatment with potassium permanganate, sodium periodate in t-butyl alcohol at 80° C. to produce the corresponding seco-acid 9. Treatment of the secoacid 9 with an appropriate amine e.g., methylamine hydrochloride and sodium acetate in ethylene glycol at 180° C., yields the 4-aza-androst-5-en-3-one 10. The TBS protecting group is then removed e.g., by aqueous HF in acetonitrile at 0° C., to yield the 17-B alcohol 11. This in turn is selectively reduced to remove the 5-delta double bond to produce the 5α-hydrogen compound 12.

FLOWSHEET C
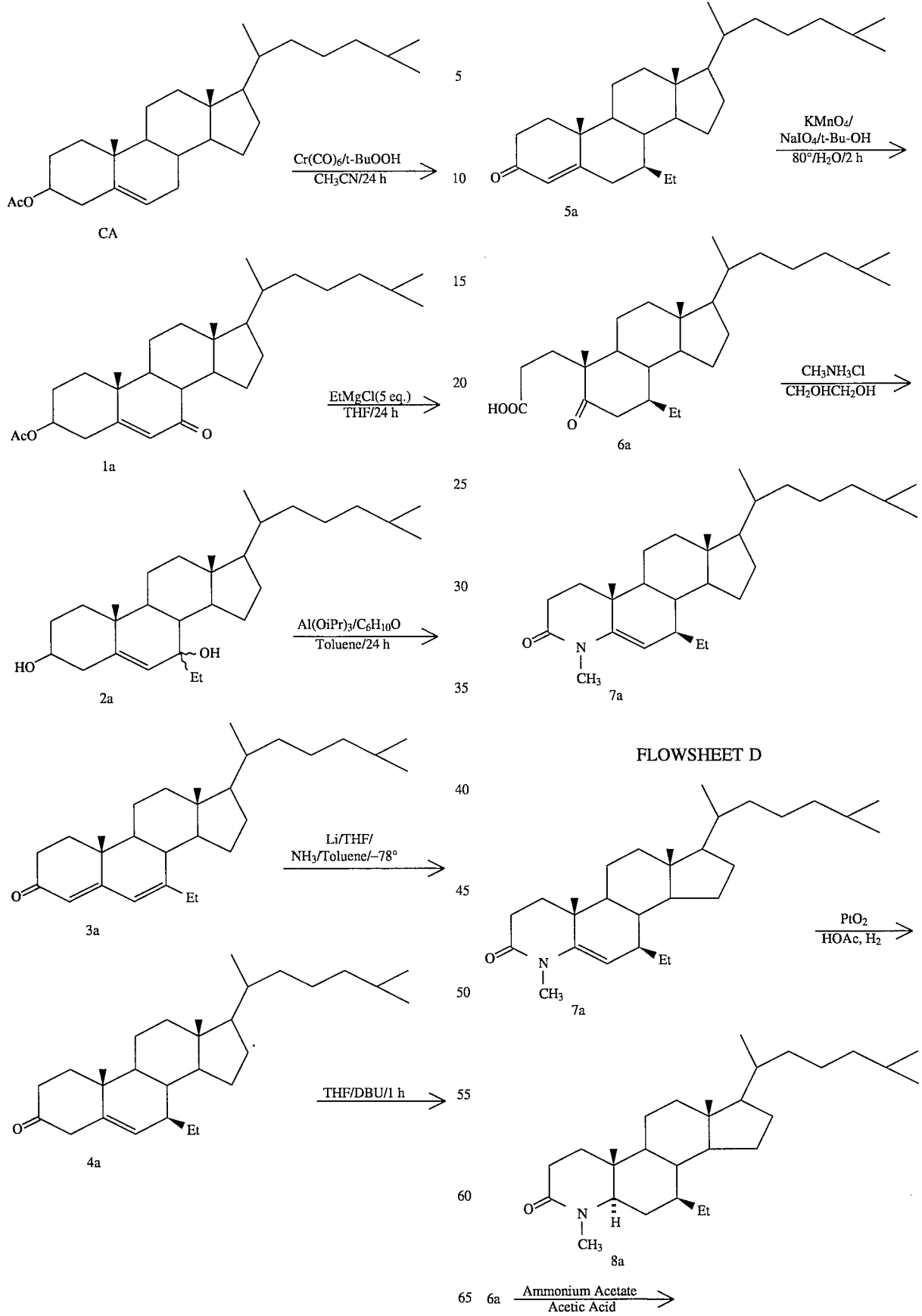
FLOWSHEET D
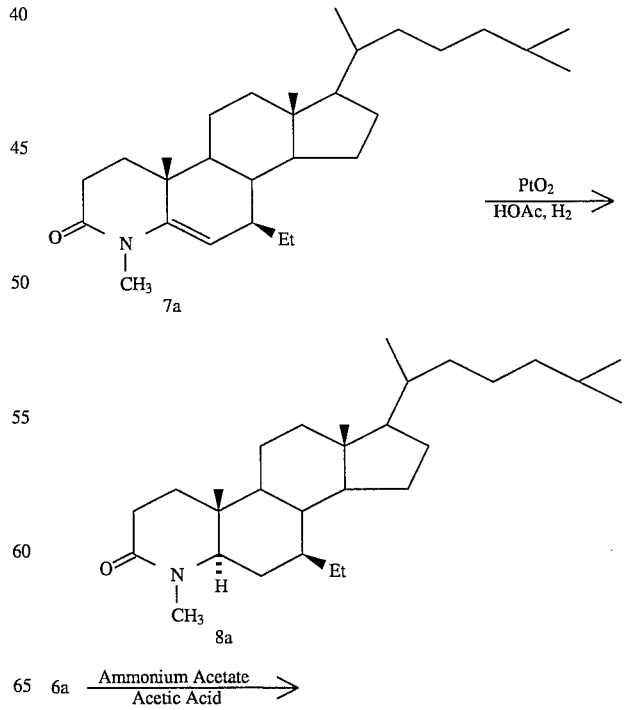

-continued

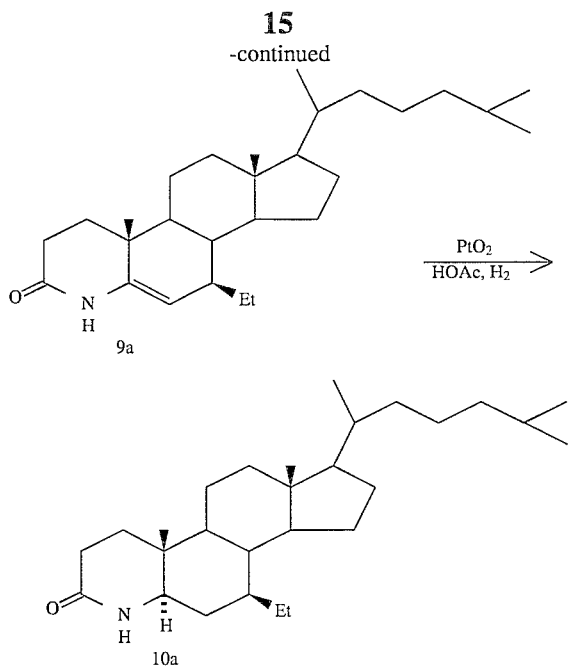

7-Beta-Ethyl-Cholestane Analogues

The 7-ethyl substituent is introduced into the cholestane series as illustrated in Flowsheets C and D by the same analogous procedure as described in the General Flowsheets and A and B.

The starting cholesteryl acetate CA is available commercially (Aldrich). This is treated using the analogous chromium hexacarbonyl/hydrogen t-butylperoxide/acetonitrile oxidation procedure (described in JCS Perkin Trans. 1985, p. 267 by A. J. Pearson) to yield the 3-acetoxy-cholest-5-en-7-one 1a. This can be reacted with an alkyl Grignard reagent, e.g. ethyl magnesium chloride to form the adduct 2a. This is oxidized under Oppenauer conditions to yield the dienone 3a, which then can undergo metal-ammonia reduction to yield the 7β-ethyl-5-en-3-one, 4a. This is isomerized using DBU to the 4-en-3-one, 5a, which is oxidized to open Ring A to yield the seco-acid 6a. This can be treated with amines, e.g. methylamine, to yield the A-ring closed 4-methyl-4-aza compound 7a. This in turn can be catalytically hydrogenated to yield the 7-ethyl-5-alpha-4-methyl-4-aza-cholestan-3-one, 8a.

Similarly, by treatment of the seco-acid 6a with ammonium acetate/acetic acid, the corresponding 4-NH analog 9a, is produced which can be catalytically hydrogenated to yield the 7-beta-ethyl-5α-4-aza-cholestan-3-one, 10a.

The above defined 7-substituents can be introduced into all of the compounds defined for the 17-A group herein by appropriate analogous procedures.

The following examples are illustrative of representative embodiments of this invention and should not be construed to be limits on the scope or spirit of the instant invention.

The Rf values cited were carried out on standard thin layer chromatographic Si gel plates. The elution solvent system used is given in the parentheses following the Rf value.

The mass spectral values are given either as FAB, i.e., fast atom bombardment, and are reported as (M+1) molecular ion peaks, being the molecular weight plus one atomic mass unit. The electron impact (EI) mass spectrum values are reported as molecular ion peaks and are indicated in parentheses, either being (M) or (M+2), the molecular weight, MW, or the MW plus two atomic units.

The nuclear magnetic resonance data was taken at 400 MHz in CDCl$_3$ and is tabulated for unique proton values of each compound at the end of the Examples. The coupling constant 3 is given in Hertz (Hz) units.

EXAMPLE 1

Synthesis of 3-Acetoxy-Androst-5-en-17-ol (2)

To a solution of 100 mg. (0.303 mmol) of 3-acetoxy-androst-5-en-17-one, 1, in 3 ml EtOH at −10° C., was added 22.9 mg (0.606 mmol) of sodium borohydride with stirring. After the reaction mixture was stirred for one and ½ hours, the mixture was diluted with 10 ml water, the ethanol solvent removed under vaccum, and the residue extracted with ethyl acetate. The organic layer was washed with aqueous Na$_2$CO$_3$, brine, dried over sodium sulfate and concentrated to leave a residue of crude title compound 2. Proton NMR confirmed the assigned structure.

EXAMPLE 2

Synthesis of 3-Acetoxy-Androst-5-en-17-ol, 17-t-butyldimethylsilyl ether (3)

To a solution of the androstan-17-ol, 2. from Example 1, being 4.5 g (13.55 mmol) in 50 ml. dimethylformamide at 23° C. was added 2.76 g (40.65 mmol) imidazole followed by 3.063 g (20.32 mmol) of t-butyldimethylsilyl chloride. The reaction mixture was stirred and a solid began to precipitate. Twenty additional ml of DMF were added was and the mixture further stirred overnight. The mixture was poured into 1 liter water, the solid filtered and washed with water. The solid was dissolved in ethylacetate, the organic layer washed with brine and dried over sodium sulfate, concentrated to yield the silyl protected 7-ol title compound 3. The proton NMR confirmed the assigned structure.

EXAMPLE 3

Synthesis of 3-Acetoxy-Androst-5-ene-7-one-17β-ol, 17-t-butyldimethylsilyl ether (4)

To a solution of the TBMS protected 17-ol 3 from Example 2, being 5.6 g (12.55 mmol) in 100 ml acetonitrile at 23° C. was added 90% t-butyl hydrogen peroxide, 3.958 g (43.92 mol), and 138 mg chromium hexacarbonyl. After refluxing the mixture under nitrogen for 24 hours, the reaction mixture was poured into one liter water, solid was filtered, the residue washed with 500 ml water and the residue dissolved in 350 ml methylene chloride. The organic layer was washed with brine, dried over sodium sulfate and concentrated to yield crude material. Thin layer chromatography (3:1 hexane/ethyl acetate on silica gel) showed the presence of starting material. The solid was purified by column chromatography over silica gel by elution with 7% ethyl acetate/hexane to yield the title compound 4. Proton NMR confirmed the assigned structure.

EXAMPLE 4

Synthesis of
3,7-Dihydroxy-7-methyl-Androst-5-en-17β-ol,
17-TBMS ether (5)

To a solution of the product 4 from Example 3, being 440 mg. (0.956 mmol) in dry tetrahydrofuran at 0° C. was added dropwise methyl magnesium chloride over 5–10 minutes. The reaction mixture was then allowed to stir at room temperature for 24 hours, then poured into saturated aqueous ammonium chloride. The THF solvent was removed under vacuum and the aqueous phase extracted with ethyl acetate. The organic layer was washed with brine, dried, concentrated to yield crude product. Proton NMR confirmed the assigned structure of the title compound 5 which was used in the next step without further purification.

EXAMPLE 5

Synthesis of
7-methyl-Androst-4,6-dien-3-one-17-ol,
17-t-butyldimethylsilyl ether (6)

The above Grignard product 5, 3.5 g. (7.142 mmol) was dissolved in 50 ml toluene/50 ml. cyclohexanone and 20 ml of solvent distilled off under vacuum. To this was added 4.54 g. aluminum isopropoxide and the reaction mixture refluxed overnight for 15 hours. The mixture was cooled, diluted with ethyl acetate, washed with sodium potassium tartarate, brine, and the organic layer was concentrated under vacuum and the residue steam distilled. The residue was extracted with ethyl acetate, washed with brine, dried and purified by column chromatography on silica gel, eluting with 5% EtOAc/hexane to yield the title compound 6.

EXAMPLE 6

Synthesis of 7β-Methyl-Androst-5-en-3-one-17-ol,
t-Butyldimethylsilyl ether (7)

To a solution of 370 mg of 6, from Example 5, in 5.5 ml ammonia, 1 ml THF, 1 ml. toluene, was added 50 mg. of metallic lithium in small pieces. After stirring the blue solution for 2 hours, a solution of 1,2-dibromethane in 2 ml THF was added. After stirring the solution at −78° C. for 10 minutes, 250 mg of ammonium chloride was added and the mixture stirred for 10 minutes. The excess ammonia was removed by evaporation under a nitrogen steam. The reaction mixture was diluted with brine, extracted with ethyl acetate. The organic layer was washed with brine, dried and concentrated to yield crude material 7 which was used as such in Example 7.

EXAMPLE 7

Synthesis of 7β-Methyl-Androst-4-en-3-on-17-ol,
t-Butyldimethylsilyl ether, (8)

To a solution of 2, from Example 6, being 432 mg in 4 ml THF was added 150 microliters DBU (1,8-diazabicyclo[5.4,0]undec-7-ene under nitrogen with stirring. The mixture was refluxed for 1.5 hours, then cooled, diluted with $NH_4Cl$ solution. The solvent THF was removed under vacuum and the residue extracted with ethyl acetate. The organic layer was washed with brine, dried and concentrated under reduced pressure to yield crude material. The titled product B was purified by chromatography on silica gel using 10% EtOAc/hexane as eluant.

EXAMPLE 8

Synthesis of
17β-(t-butyldimethylsilyloxy)-7B-methyl-5-oxo-A-nor-
3,5-secoandrostan-3-oic acid, (9)

To a solution of 884 mg of 8 in 15 ml. t-butyl alcohol at 80° C. was added 248 mg sodium carbonate in 1.5 ml water followed by a dropwise addition over 15–20 minutes of a mixture of 2.273 g sodium periodate with 16.8 mg potassium permanganate in 8 ml. water. The reaction mixture was heated at 80° C. for 2 hours, cooled, filtered, the residue washed with water, and then the extract concentrated under vaccum. The extract was acidified with aqueous HCl, extracted with ethyl acetate and the organic layer washed with aqueous $NaHSO_3$, brine, dried and concentrated to yield crude 9. The proton NMR confirmed the assigned structure.

EXAMPLE 9

Synthesis of
4,7-Dimethyl-4-aza-Androst-5-en-3-one-17-ol,
t-butyldimethylsilyl ether, (10)

To a solution of 9, 840 mg in 5 ml ethylene glycol was added 1.5 g sodium acetate and 737 mg. methylamine hydrochloride. After stirring the reaction mixture 4 hours at 180° C., the mixture was cooled, diluted with water, extracted with ethyl acetate, dried and concentrated to afford crude title compound 10. Proton NMR confirmed the assigned structure.

EXAMPLE 10

Synthesis of
4,7-Dimethyl-4-aza-Androst-5-en-3-one-17-ol (11)

To a solution of 700 mg of 10 from Example 9, in 20 ml of acetonitrile at 0° C. was added 500 microliters aqueous HF. After stirring the reaction mixture for one hour, the HF was neutralized with aqueous sodium carbonate, diluted with water, acetonitrile removed under vacuum, and the residue extracted with ethyl acetate. The organic layer was dried, concentrated to give crude title compound 11 which was further purified by preparative chromatography on silica gel using 3:1 chloroform/acetone.

EXAMPLE 11

Synthesis of
4,7-dimethyl-a-aza-androstan-3-one-17-ol, (12)

To a solution of 11 from Example 10, being 350 mg in 10ml acetic acid was added 100 mg catalytic platinum dioxide and the resulting mixture was evacuated and flushed with hydrogen. The reaction was shaken overnight at room temperature under 40 Psig hydrogen pressure. The solution was filtered and concentrated to a residue. The residue was worked up with ethyl acetate, the organic layer was then concentrated under vacuum, diluted with ethyl acetate, washed with aqueous $NaHCO_3$, brine, dried, concentrated to yield the title compound 12. Mass Spec: 320,(M+1).

The following Table lists the unique proton NMR values (400 MHz in $CDCl_3$) for each compound. The data are reported as: s=singlet, d=doublet, m=multiplet, J=coupling constant. The absorption values are given del (δ) units and are illustrated for the C-18, C-19 and C-21 angular ring methyl protons and protons associated with unique portions of the molecule.

The numbering of the steroid is given by the following structure:

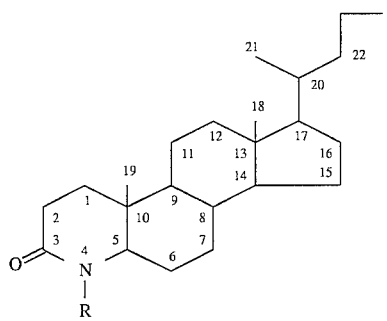

| Compound No. | C-18 CH$_3$ | C-19 CH$_3$ | Others |
| --- | --- | --- | --- |
| 2 | 0.72 | 1.02 | 3OAc, 3H, s, 2.02<br>17H, 1H, t, 3.65, J=8.5 |
| 3 | 0.70 | 1.02 | 3OAc, 3H, s, 2.02<br>17H, 1H, t, 3.55, J=8.5 |
| 4 | 0.72 | 1.21 | 3OAc, 3H, s, 2.04<br>17H, 1H, t, 3.55 J=8.5 |
| 5 | 0.72 | 0.95<br>1.20 | 7Me, 3H, s, 1.12<br>1.21<br>17H, 1H, m, 3.55 |
| 6 | 0.80 | 1.08 | 7Me, 3H, s, 1.9<br>6H, 1H, s, 5.68<br>4H, 1H, s, 5.92 |
| 7 | 0.72 | 1.12 | 7Me, 3H, d, 0.96 J=6.6<br>6H, 1H, m, 5.08 |
| 8 | 0.72 | 1.17 | 7Me, 3H, d, 1.03 J=6.5<br>4H, 1H, s, 5.68 |
| 9 | 0.72 | 1.04 | 7Me, 3H, d, 0.95 J=6.5 |
| 10 | 0.72 | 1.02 | 7Me, 3H, d, 1.04 J=6.5<br>6H, 1H, d, 4.78 J=3 |
| 11 | 0.78 | 1.02 | 7Me, 3H, d, 1.06, J=6.5<br>6H, 1H, d, 4.79, J=3 |
| 12 | 0.74 | 0.86 | 7Me, 3H, d, 1.02, J=6.5<br>5H, 1H, dd, 3.10 J=4.5 J=13.5 |
| 8a | 0.690 | 0.830 | 21-CH$_3$, d, 0.900 J=7<br>N—CH$_3$, s, 2.93 |
| 10a | 0.675 | 0.808 | 21-CH$_3$, d, 0.893 J=7<br>5H, m, 2.97–3.13 |

What is claimed is:

1. A process comprising the step of:
   (a) contacting the compound IV,

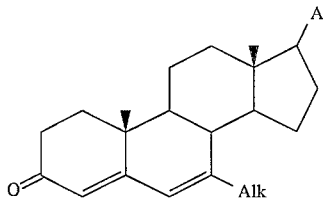

where Alk is $C_1$–$C_4$ alkyl, allyl, and $C_3$–$C_6$ cycloalkyl; and
where A is a substituent inert under the reaction conditions selected from —H, t-butyl dimethyl silyloxy, hydroxy, acetylamino, amino, $C_{1-10}$alkyl, phenyl substituted $C_{1-10}$alkyl, pyridyl substituted $C_{1-10}$alkyl, carboxylic ester, carboxamide, carboxylic acid, and carbamate;
with a reducing system comprised of: metallic lithium and liquid ammonia in an inert organic solvent therefor at a temperature in the range of about –45° to –78° C. for a sufficient time to stereoselectively produce the 7β compound V:

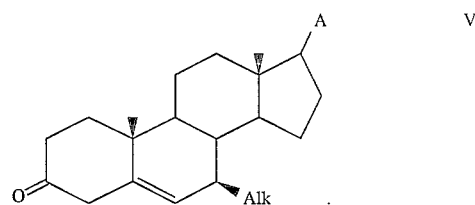

2. The process of claim 1 further comprising the step of
   (b) contacting isolated compound V with a double bond isomerization agent selected from DBU (1,8-diazabicyclo[5.4.0]undec-7-ene), diisopropylethylamine and DBN (1,5-diazabicyclo[4.3.0]non-5-ene), in an inert organic solvent therefor, at a temperature of 40° to 65° C., under conditions in which the radical A is inert, for a sufficient time to form the isomerized compound VI:

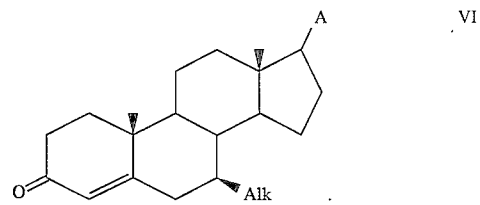

3. The process of claim 1 further comprising the step of:
   (c) contacting isolated compound VI with an oxidizing agent selected from potassium permanganate, sodium periodate, ruthenium tetraoxide and ozone in an inert solvent therefor, at a temperature in the range of 23° to 80° C., under conditions in which radical A is inert, for a sufficient time to form the seco acid VII:

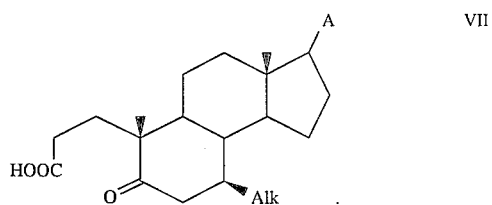

4. The process of claim 3 further comprising the step of:
   (d) contacting the isolated seco acid compound VII with an amine of the formula: R—NH$_2$, wherein R is H, $C_1$–$C_4$ alkyl, benzyl or allyl, at a temperature of from 100° to 200° C. in an inert solvent therefor, under conditions in which A is inert, to form the 4-aza-steroid VIII:

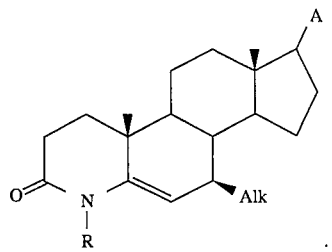

VIII

5. The process of claim 4 further comprising the step of:
(e) contacting isolated VIII wherein R is $CH_3$ and Alk is selected from $C_1$–$C_4$ alkyl, and $C_3$–$C_6$ cycloalkyl with a platinum catalyst in an inert organic solvent, at room temperature, under conditions where A is inert, for a sufficient time to form the 7-Alk 4-aza steroid IX:

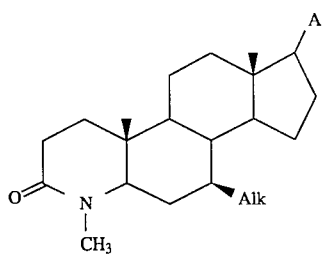

IX

6. The process of claim 1 in which Alk is methyl.
7. A process comprising the steps of:
(a) contacting the compound IV, where Alk is

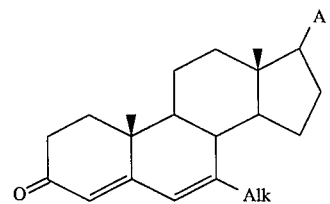

IV $C_1$–$C_4$ alkyl, and $C_3$–$C_6$ cycloalkyl; and
where A is a substituent inert under the reaction conditions selected from —H, t-butyl dimethyl silyloxy, hydroxy, acetylamino, amino, $C_{1-10}$alkyl, phenyl substituted $C_{1-10}$alkyl, pyridyl substituted $C_{1-10}$alkyl, carboxylic ester, carboxamide, carboxylic acid, and carbamate; with a reducing system comprised of: metallic lithium and liquid ammonia in an inert organic solvent therefor at a temperature in the range of about −78° to −45° C. for a sufficient time to stereoselectively produce the 7β compound V:

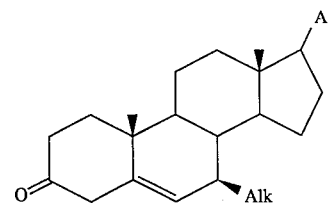

V (b) contacting isolated compound V with a double bond isomerization agent in an inert organic solvent therefor, at a temperature of 40° to 65° C., under conditions in which the radical A is inert, for sufficient time to form the isomerized compound VI:

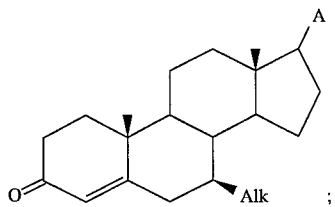

VI (c) contacting isolated compound VI with an oxidizing agent selected from potassium permanganate, sodium periodate, ruthenium tetraoxide and ozone in an inert solvent therefor, at a temperature in the range of 23° to 80° C., under conditions in which radical A is inert, for a sufficient time to form the seco acid VII:

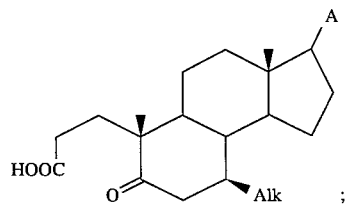

VII (d) contacting the isolated seco acid compound VII with an amine of the formula R—$NH_2$ wherein R is H, $C_1$–$C_4$ alkyl, benzyl or allyl, at a temperature of from 100° to 200° C. in an inert solvent therefor, under conditions in which A is inert to form the 4-aza-steroid VIII:

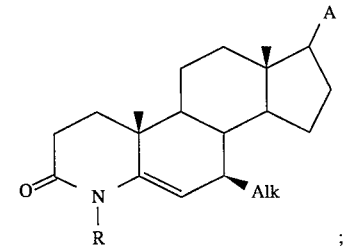

VIII (e) contacting isolated VIII with a platinum catalyst in an inert organic solvent, at room temperature, under conditions where A is inert, for a sufficient time to form the 7-Alk 4-aza steroid IX:

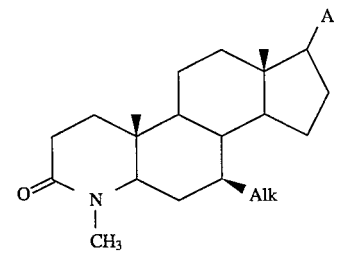

IX

8. The process of claim 1 wherein A is —OTBS or 6-methyl-hept-2-yl.
9. The process of claim 1 wherein A is 6-methyl-hept-2-yl.

* * * * *